United States Patent [19]

Kroeger

[11] 4,137,573

[45] Feb. 6, 1979

[54] URINE SPECIMEN COLLECTOR

[76] Inventor: Daniel E. Kroeger, 2029 167th Ave., San Leandro, Calif. 94578

[21] Appl. No.: 856,153

[22] Filed: Nov. 30, 1977

Related U.S. Application Data

[63] Continuation of Ser. No. 663,023, Mar. 2, 1976, abandoned.

[51] Int. Cl.² ...................... E03D 13/00; A61B 10/00
[52] U.S. Cl. .................................... 4/144.1; 128/2 F; 248/214
[58] Field of Search ..................... 4/301, 144.1, 144.2, 4/216, 217, 231, 248; 128/2 F, 295; 222/108; 248/214, 215, 291, 301

[56] References Cited

U.S. PATENT DOCUMENTS

| 2,673,059 | 3/1954 | Lustig | 248/219 X |
| 2,920,853 | 1/1960 | Bufogle | 248/214 |
| 3,290,699 | 12/1966 | Weinstein | 4/231 |
| 3,881,465 | 5/1975 | Raitto | 4/144.1 X |

FOREIGN PATENT DOCUMENTS

| 284866 | 2/1929 | United Kingdom | 222/108 |
| 329138 | 11/1920 | Fed. Rep. of Germany | 4/248 |

*Primary Examiner*—Stuart S. Levy
*Attorney, Agent, or Firm*—Townsend and Townsend

[57] ABSTRACT

A urine specimen collector comprising a fixture adapted to be removably installed on the rim of a water closet and including a bracket member with an inverted U-shaped clamp portion dimensioned to embrace the rim of the water closet, a downwardly extending curved leg portion for contacting the inner surface of the water closet, and an annular receptacle secured to the bracket member; and a removable liner assembly including a carrier member supported by the annular receptacle and having a central aperture in registry with the aperture in the annular receptacle and a laterally extending handle portion, and an integrally formed liner received within the central aperture and the receptacle aperture, the liner having a peripheral flange received by the upper surface of the carrier member.

The bracket member includes means extending upwardly from the top surface of the U-shaped clamp portion for providing supplemental stability for the fixture and including an upwardly extending abutment element engageable with the lower surface of the seat portion of the water closet when installed in situ.

The liner has an upper body portion extending above the peripheral flange and terminating in a rim which extends downwardly and outwardly thereof for removably receiving a locking cover member having a mating rim portion engageable with the upper body rim portion when the cover member is secured to the liner.

13 Claims, 6 Drawing Figures

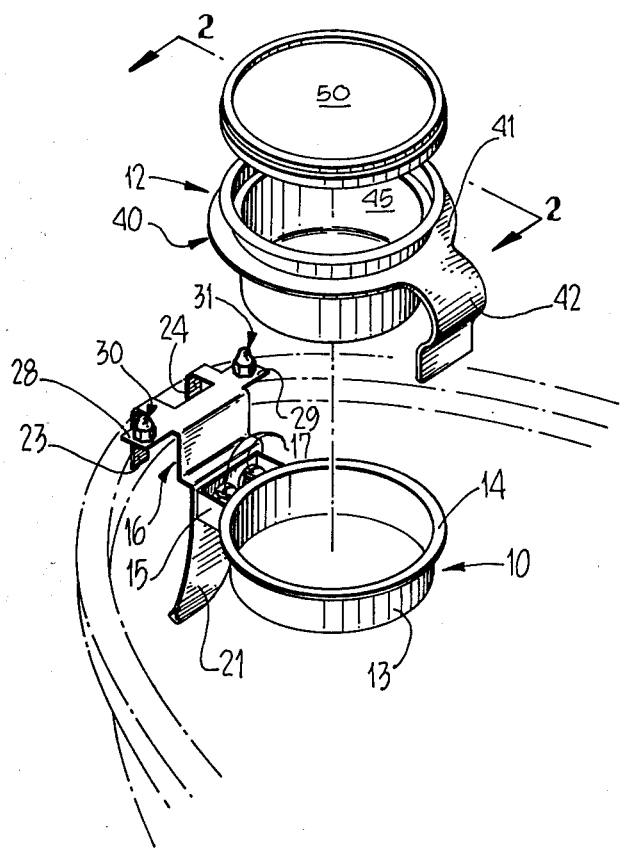
Fig_1
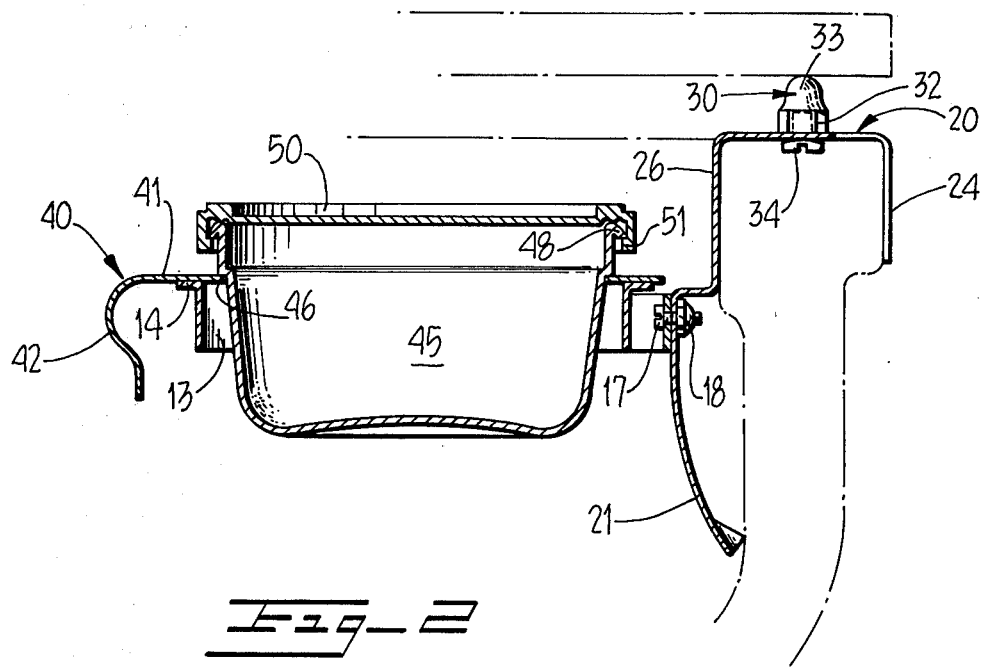
Fig_2

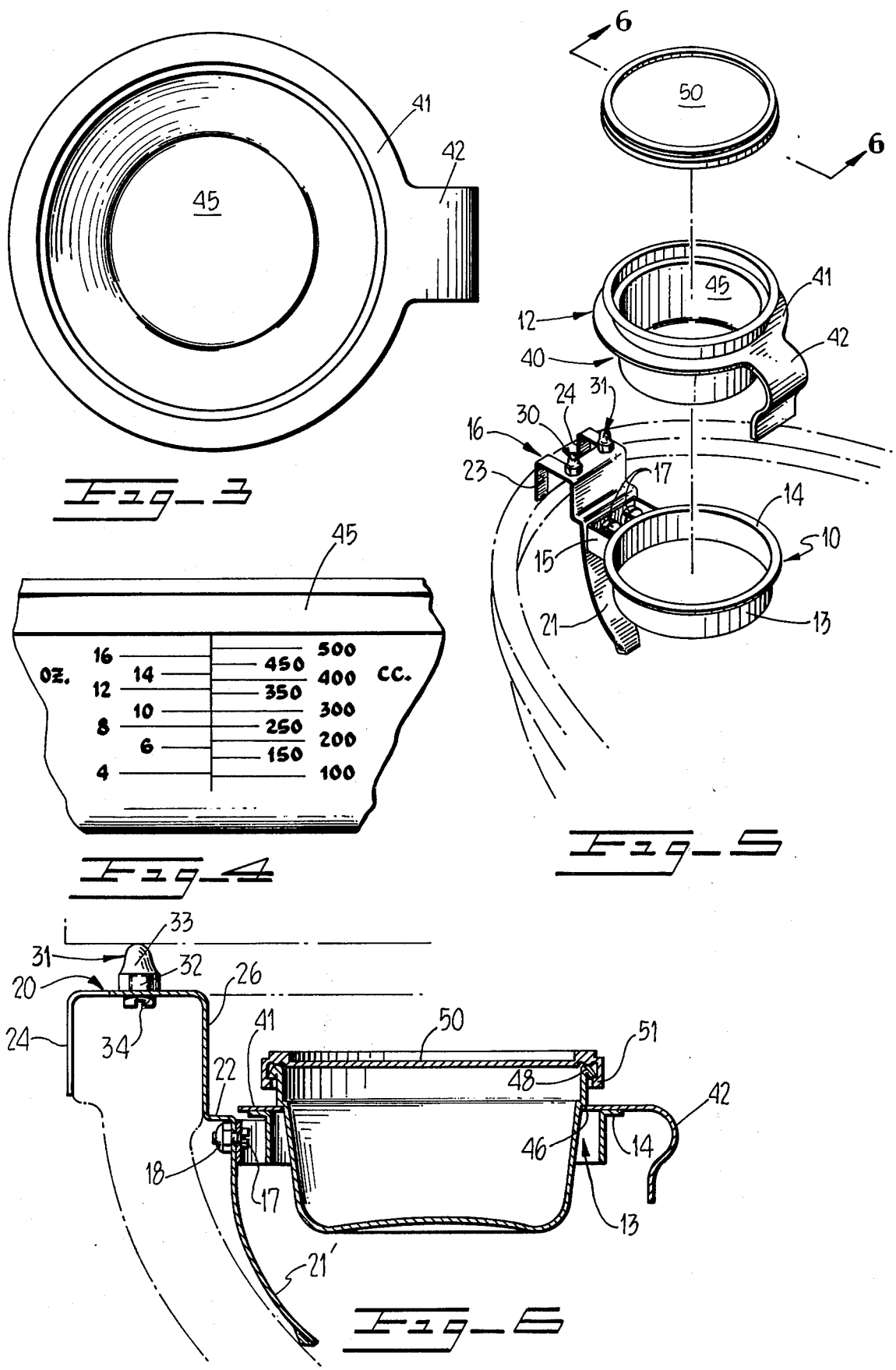

URINE SPECIMEN COLLECTOR

This is a continuation of application Ser. No. 663,023, filed Mar. 2, 1976; now abandoned.

BACKGROUND OF THE INVENTION

This invention relates to specimen collectors of the type used to collect human urine specimens.

Specimens of human wastes are frequently required for medical diagnostic testing purposes. Many types of specimen collector have been proposed, among which the disclosures of the following U.S. patents are representative: U.S. Pat. Nos. 2,560,199; 2,734,198; 3,625,654; and 3,654,638. Ideally, a urine specimen collector should be easy to install and remove, extremely inexpensive in cost, and should be designed in such a way as not to unduly obstruct the normal operation of the water closet.

Known specimen collectors suffer from one or more disadvantages which hinders their utility in most applications. Some collectors employ removable liners or containers and a companion support fixture which is inherently awkward to install, unstable when installed or both. Others have such great size that they can effectively block the working bowl area of the water closet, which impairs the normal operation of the water closet. Other collectors utilize an adhesive substance for temporary attachment of the liner directly to the water closet surfaces, which adhesive does not readily adhere when condensation is present on the water closet surface. In addition, in such colllectors the collected specimen is readily spilled when attempting to detach the collector from the water closet surface. Still other specimen collectors are only utilizable with water closets having a predetermined shape and are thus not adapted for a use with a wide variety of water closets.

SUMMARY OF THE INVENTION

The invention comprises a urine specimen collector adapted for use in a wide variety of applications, and which is inexpensive to manufacture, easy to install and remove, and highly stable when installed, so that only a minimum of care in handling is necessary in order to avoid spilling the fluid sample collected therein.

In its broadest aspect, the invention comprises a fixture adapted to be removably installed on the rim of a water closet and includes a bracket member with an inverted generally U-shaped clamp portion adapted to embrace the rim of a water closet and a downwardly extending curved leg portion adapted to contact the inner surface of the water closet, an annular receptacle, and means for securing the annular receptacle to the bracket member; and a removable liner assembly comprising a carrier member having a central aperture in registry with the aperture in the annular receptacle and a laterally extending handle portion, the carrier member being supported on the upper surface of the annular receptacle, and an integrally formed liner having a body portion with an outer surface portion received within the central aperture and the receptacle aperture, the liner having a peripheral flange portion received by the upper surface of the carrier member. The bracket member leg portion is alternately curved outwardly or inwardly in a downward direction, depending on the contour of the inner surface of the water closet. In the preferred embodiment, the clamp portion and the leg portion of the bracket member are interconnected by a laterally extending spacer portion for optimally positioning the receptacle and the liner.

The bracket member includes means extending upwardly from the top surface of the U-shaped clamp portion for providing supplemental stability for the fixture, this means including an upwardly extending abutment element adapted for engagement with the lower surface of the seat portion of the water closet when installed in situ.

The liner further includes an upper body portion extending above the peripheral flange portion thereof and terminating in a rim portion extending downwardly and outwardly of the upper body portion for removably receiving a locking cover member having a locking rim portion for engagement with the upper body rim portion when the cover member is secured to the liner.

For the fuller understanding of the nature and advantages of the invention, reference should be had to the ensuing detailed description taken in conjunction with the accompanying drawings.

BRIEF DESCRIPTION OF THE DRAWINGS

FIG. 1 is an exploded perspective view of a first embodiment of the invention;

FIG. 2 is a sectional view taken along lines 2—2 of FIG. 1;

FIG. 3 is a top plan view of the liner and carrier member of FIG. 1;

FIG. 4 is a schematic partial view of the inner wall surface of the liner;

FIG. 5 is an exploded perspective view of an alternate embodiment of the invention; and FIG. 6 is a sectional view taken along lines 6—6 of FIG. 5.

DESCRIPTION OF THE PREFERRED EMBODIMENTS

Turning now to the drawings, FIG. 1 illustrates a first embodiment of the invention. As seen in this figure, a fixture 10 for removably receiving a liner assembly 12 includes an annular receptacle portion 13 having an upper peripheral flange portion 14 and a generally U-shaped member 15 secured to a bracket member 16 by means of a pair of mating bolts 17 and nuts 18 (FIG. 2). Member 15 is secured to the outer wall of portion 13 in any convenient fashion, e.g. by welding or using suitable nuts and bolts. Bracket member 16 is an integrally formed member having an upper inverted U-shaped portion 20, a curved leg portion 21, and an intermediate spacer portion 22. U-shaped portion 20 includes a pair of outwardly and downwardly extending leg members 23, 24, and is dimensioned to embrace the peripheral lip of a conventional water closet or commode illustrated in phantom in FIGS. 1 and 2 so that receptacle 10 may be readily removably attached thereto. Spacer portion 22 provides sufficient clearance from the inner edge of the commode lip to accommodate liner assembly 12 and receptacle 13 and to position these members in an optimum location for receiving specimens. Leg portion 21 is curved so that the end portion thereof bears against the inner wall surface of the water closet basin in order to provide stable support for liner assembly 12 and receptacle 13 in concert with U-shaped portion 20 when bracket member 16 is installed in the water closet. Preferably, bracket member 16 is fabricated from stainless steel of sufficient gauge to enable leg portion 21 to provide a slightly resilient support in order to account for variation in the inner wall surface taper of different water closets.

Secured to a pair of oppositely extending tab portions 28, 29 of bracket member 16 are a pair of upwardly extending abutment members 30, 31. As best shown in FIG. 2, these abutment members perferably comprise an internally threaded nut 32 terminating in a rounded free end 33 and an externally threaded bolt 34 passed through an aperture (not shown) in the corresponding tab portion. The height of the end portion 33 of nut 32 above the top surface of bracket member 16 is chosen so that abutting engagement is provided with the lower surface of the seat portion of the commode when the seat portion is in the lowered position. This arrangement provides supplemental stability to the apparatus when in use. Lateral spacing of members 30, 31 in the FIGS. 1 and 2 embodiment is chosen to be greater than the open span between the front portion of a split-type water closet seat.

Liner assembly 12 comprises a carrier member generally designated by reference numeral 40 and including a thin ring-shaped main body portion 41 terminating in an integrally formed downwardly turned handle portion 42, and a liner 45 having a lower body portion with an outer diameter smaller than the inner diameter of the central aperture in carrier member 40 and an enlarged upper body portion joined to the lower body portion and forming a flange surface 46 resting on the upper surface of main body portion 41 of carrier member 40. The upper body portion terminates in an outwardly and downwardly extending rim portion 48 designed for locking engagement with the rim portion 51 of a removable cover member 50. As shown in FIG. 4, a graduated scale calibrated in ounces and cubic centimeters is printed on the inner wall surface of liner 45 to facilitate quantitative measurement of a urine specimen. Liner 45 and cover member 50 may comprise a conventional, commercially available container fabricated from molded plastic, the liner being modified to provide the graduated scale and any other printed matter as desired.

In use, receptacle 13 is secured to bracket member 16 and abutment elements 30, 31 are installed. After assembly, fixture 10 is installed on the rim of the water closet by engaging U-shaped portion 20 of bracket member 16 on the rim at the front end thereof. After installation of fixture 10, the device is ready for use, which proceeds by inserting a liner 45 into carrier member 40 and placing the assembly 12 onto receptacle 13. This may be done either by the patient or a medical professional. After the specimen has been collected, the liner assembly 12 is removed from receptacle 13, liner 45 is removed from carrier member 40, cover member 50 is attached and the apparatus is ready for use with a new liner 45.

FIGS. 5 and 6 illustrate an alternate embodiment of the invention employing a modified bracket member 16 for use with water closets having a different inner surface contour. As best shown in FIG. 6, leg portion 21' of bracket member 16 is curved inwardly in the downward direction in this embodiment to accommodate the steeper inward taper of the inner wall surface of the water closet depicted in phantom. This is in contrast with the embodiment of FIGS. 1 and 2 in which leg portion 21 is curved outwardly in the downward direction.

Also shown in FIGS. 5 and 6 is an alternate spacing arrangement for abutment elements 30, 31 which is preferred for use with water closets having solid seat portions, i.e. non-split seat portions. As seen in FIG. 5, elements 30, 31 are more closely spaced together in this embodiment than in the embodiment of FIGS. 1 and 2. Assembly, installation and use of the embodiment of FIGS. 5 and 6 proceeds in essentially the same manner as that described above.

Preferably receptacle 13, bracket 15, bracket member 16, carrier member 40 and the fastening elements are all fabricated from stainless steel so that they may be passed through an autoclave for sterilization purposes without corrosion. Other equivalent materials will occur to those skilled in the art.

As will now be apparent to those skilled in the art, both the receptacle and liner portions of the invention may be fabricated at an extremely low cost and thus the invention is particularly well suited for high volume applications, such as in hospitals, medical clinics and the like. Further, the invention may be quickly installed by any person without the requirement of any technical skill and may be readily removed when no longer required. In addition, liners 45 and cover members 50 may be compactly stored by independent stacking prior to use, and are readily disposable. Locking cover member 50 enables storage of fresh specimens for considerable periods without deterioration and reduces environmental odors from specimens awaiting analysis. Lastly, fixture 10 is highly stable when installed and not subject to tipping which facilitates handling, installation and removal of liner assembly 12 without spilling of the contents.

The invention is also dimensioned in such a manner that the normal bowl area of the associated water closet is not unduly impaired when the apparatus is installed. In an actual embodiment of the invention, the inner diameter of receptacle 13 is less than 5 inches and the axial dimension thereof is approximately 1 inch. Thus, even with fixture 10 installed on the water closet, the water closet is still available for emergency use if required.

While the above provides a full and complete disclosure of the preferred embodiments of the invention, various modifications, alternate constructions and equivalents may be employed without departing from the true spirit and scope of the invention. For example, separate abutment members 30, 31 may be omitted if desired and tab portions 28, 29 shown in FIG. 1 may be lengthened and bent upwardly and inwardly to provide a similar function. Therefor, the above description and illustration should not be construed as limiting the scope of the invention which is defined by the appended claims.

What is claimed is:

1. A urine specimen collector adapted to be removably secured to a water closet, said collector comprising:

a fixture adapted to be removably secured to said water closet, said fixture having a bracket member with an inverted generally U-shaped clamp portion adapted to embrace the rim of said water closet and a downwardly extending leg portion adapted to contact the inner surface of said water closet, an annular receptacle, means for securing said receptacle to said bracket member and means for providing supplemental stability for said collector;

said bracket member including a spacer portion interconnecting said clamp portion and said leg portion, said spacer portion extending laterally from said clamp portion to said leg portion in the diection of said receptacle;

said securing means including a generally U-shaped member attached to and extending laterally of said receptacle;

said bracket member and said receptacle being fabricated from a sterilizable material; and a removable liner assembly including a carrier member removably supported by said receptacle and having a handle portion extending generally laterally thereof and a central aperture in substantial registry with the aperture in said annular receptacle, and a separate removable disposable liner having a body portion with an outer surface portion received within said central aperture and said receptacle aperture, said liner having a peripheral flange portion received by the upper surface of said carrier member and a bottom surface;

said leg portion of said bracket member extending below said receptacle and said bottom surface of said liner to provide support therefor when placed in contact with said inner surface of said water closet.

2. The combination of claim 1 wherein said bracket member leg portion is curved outwardly in the downward direction.

3. The combination of claim 1 wherein said bracket member leg portion is curved inwardly in the downward direction.

4. The combination of claim 1 wherein said annular receptacle comprises a substantially cylindrical body portion terminating in a peripheral flange portion at the upper end thereof.

5. The combination of claim 1 wherein said leg portion is provided with a pair of spaced apertures and said U-shaped member has a pair of spaced apertures in registry with said spaced apertures in said leg portion, and further including a plurality of complementary threaded members extending through said apertures in fastening engagement.

6. The combination of claim 1 wherein said means for providing supplemental stability comprises at least one abutment element extending upwardly from the upper surface of said clamp portion a sufficient distance to provide abutting engagement with the seat portion of said water closet.

7. The combination of claim 1 wherein said liner includes an upper body portion extending above said peripheral flange portion and terminating in a rim portion adapted to removably receive a cover member.

8. The combination of claim 7 wherein said rim portion extends downwardly and outwardly of said upper body portion, and further including a generally circular cover member having a locking rim portion for engagement with said upper body rim portion when said cover member is secured to said liner.

9. A fixture adapted to be removably secured to a water closet for use with a removable liner for collecting a urine specimen, said fixture comprising:

a bracket member having an inverted generally U-shaped clamp portion adapted to embrace the rim of said water closet, a downwardly extending leg portion adapted to contact the inner surface of said water closet and a laterally extending spacer portion interconnecting said clamp portion and said leg portion;

an annular receptacle;

means for securing said receptacle to said bracket member, said securing means including a generally U-shaped member attached to and extending laterally of said receptacle; and means for providing supplemental stability for said fixture comprising an abutment element extending upwardly from the upper surface of said clamp portion a sufficient distance to provide abutting engagement with the seat portion of said water closet;

said leg portion of said bracket member extending below said receptacle to provide support therefor when placed in contact with said inner surface of said water closet;

said spacer portion extending from said clamp portion to said leg portion in the direction of said receptacle;

said bracket member and said receptacle being fabricated from a sterilizable material.

10. The combination of claim 9 wherein said bracket member leg portion is curved outwardly in the downward direction.

11. The combination of claim 9 wherein said bracket member leg portion is curved inwardly in the downward direction.

12. The combination of claim 9 wherein said annular receptacle comprises a substantially cylindrical body portion terminating in a peripheral flange portion at the upper end thereof.

13. The combination of claim 9 wherein said leg portion is provided with a pair of spaced apertures and wherein said U-shaped member has a pair of spaced apertures in registry with said spaced apertures in said leg portion, and further including a plurality of complementary threaded members extending through said apertures in fastening engagement.

* * * * *